(12) United States Patent
Lin et al.

(10) Patent No.: US 6,512,122 B2
(45) Date of Patent: Jan. 28, 2003

(54) HETARYLBENZENE COMPOUNDS

(75) Inventors: Jiann T'suen Lin, Taipei (TW); Iuan-Yuan Wu, Taipei (TW); Yu-Tai Tao, Taipei (TW); E. Balasubramaniam, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/991,488

(22) Filed: Nov. 21, 2001

(65) Prior Publication Data

US 2002/0115870 A1 Aug. 22, 2002

Related U.S. Application Data

(60) Provisional application No. 60/252,488, filed on Nov. 21, 2000.

(51) Int. Cl.[7] .................................... C07D 209/82
(52) U.S. Cl. .................... 548/440; 548/518; 549/59; 549/472
(58) Field of Search ................. 548/440, 518; 549/59, 472

(56) References Cited

U.S. PATENT DOCUMENTS

| 5,077,142 A | * 12/1991 | Sakon et al. ............. 428/690 |
| 5,840,217 A | 11/1998 | Lupo et al. ............... 252/583 |
| 5,859,211 A | 1/1999 | Kreuder et al. ........... 528/403 |

OTHER PUBLICATIONS

Salbeck, et al. *Low molecular organic glasses for blue electroluminescence.* Synthetic Metals, vol. 91, 1997, pp. 209–215.
Weinfurtner, et al. *Novel amorphous molecular materials for organic light–emitting devices.* SPIE, vol. 3476, Jul. 1998, pp. 40–48.
Salbeck, et al. *Spiro Linked Compounds For Use As Active Materials In Organic Light Emitting Diodes.* Macromol. Symp. vol. 125, 1997, pp.121–132.
Oldham, Jr., et al. *Synthesis, Spectroscopy, and Morphology of Tetrastilbenoidmethanes.* J. Am. Chem. Soc., vol. 120, 1998, pp. 2987–2988.
Wang, et al. *Synthesis, Morphology, and Optical Properties of Tetrahedral Oligo(phenylenevinylene) Materials.* J. Am. Chem Soc., vol. 122, 2000, pp. 5695–5709.

\* cited by examiner

*Primary Examiner*—Joseph K. McKane
*Assistant Examiner*—Kamal Saeed
(74) *Attorney, Agent, or Firm*—Fish & Richardson P.C.

(57) ABSTRACT

A method of preparing a compound of formula I is described.

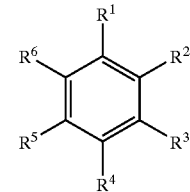

In this compound, each of $R^1$–$R^6$ is, independently,

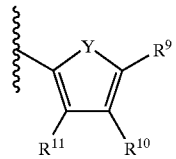

in which Y is O, S, NH, or $C(R^7)=C(R^8)$. Each of $R^7$–$R^{11}$ is, independently, H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-20}$ aryl, or substituted or unsubstituted $C_{4-20}$ heteroaryl. Alternatively, each of $R^7$–$R^{11}$ is OH, $C_{1-6}$ alkoxy, or $N(R^{12})(R^{13})$, in which each of $R^{12}$ and $R^{13}$ is, independently, H, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{6-20}$ aryl. Each of $R^7$–$R^{11}$ can also be $NO_2$, CN, or $CO_2R^{14}$, in which $R^{14}$ is H or $C_{1-6}$ alkyl.

10 Claims, No Drawings

HETARYLBENZENE COMPOUNDS

RELATED APPLICATIONS

This application claims priority to U.S. provisional application No. 60/252,488, filed on Nov. 21, 2000, the contents of which are incorporated herein by reference.

BACKGROUND

Electroluminescent (EL) devices based on organic thin layers have recently attracted much attention because of their potential uses in large-area flat-panel displays and light-emitting diodes (LED). Organic LEDs have been made with both low molecular-weight organic materials and with polymers. The performance of these devices is significantly influenced by the charge balance between electrons and holes from opposite electrodes. The charge can be balanced by using a bilayer structure including a hole transporting layer and an electron transporting layer. One or both of these layers can be luminescent.

An important quality of organic EL materials is their durability, i.e., thermal and morphological stability. Thus, it is desirable that organic EL materials are not only light-emitting and hole transporting, but also robust.

SUMMARY

The hexasubstituted benzene compounds of the invention are useful as hole transporting, green-light-emitting molecules with high glass transition temperatures. These compounds have a number of qualities that make them useful in electroluminescence devices.

In one aspect, the invention features a method of preparing a compound of formula I:

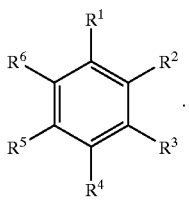

Each of $R^1$–$R^6$ is, independently,

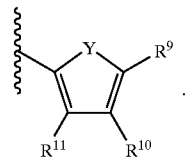

Y is O, S, NH, or $C(R^7)=C(R^8)$. Each of $R^7$–$R^{11}$ is, independently, H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-20}$ aryl, or substituted or unsubstituted $C_{4-20}$ heteroaryl. Alternatively, each of $R^7$–$R^{11}$ is OH, $C_{1-6}$ alkoxy, or $N(R^{12})(R^{13})$. For $N(R^{12})(R^{13})$, each of $R^{12}$ and $R^{13}$ is, independently, H, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{6-20}$ aryl. Each of $R^7$–$R^{11}$ can also be $NO_2$, CN, or $CO_2R^{14}$, in which $R^{14}$ is H or $C_{1-6}$ alkyl.

The method includes contacting a compound of formula II with a compound of formula III to form a compound of formula I. The compound of formula II is shown below:

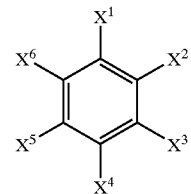

In this compound, each of $X^1$–$X^6$ is, independently, Br or I. The compound of formula III is shown below:

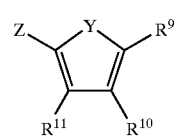

In this compound, Y and $R^7$–$R^{11}$ are as defined above and Z is ZnCl or $Sn(R^{15})(R^{16})(R^{17})$, in which each of $R^{15}$–$R^{17}$ is, independently, $C_{1-6}$ alkyl.

In some preferred embodiments, Y is O, S, or NH; each of $R^{10}$ and $R^{11}$ is H; and/or $R^9$ is $N(R^{12})(R^{13})$. Preferably, each of $R^{12}$ and $R^{13}$ is, independently, substituted or unsubstituted aryl; for example, each of $R^{12}$ and $R^{13}$ can be, independently, phenyl, tolyl, naphthyl, or pyrenyl. In other preferred embodiments, $R^9$ is carbazolyl. In other preferred embodiments, Y is $C(R^7)=C(R^8)$. In still other preferred embodiments, each of $R^{15}$–$R^{17}$ is methyl or butyl.

In another aspect, the invention features a method of forming a hexaarylbenzene; the method includes contacting a hexahalobenzene with a stannane. In preferred embodiments, the hexaarylbenzene is a hexakis-(heteroaryl) benzene. For example, the hexaaryylbenzene can be a hexakis-(thienyl)benzene, e.g., a hexakis-(carbazolylthienyl)benzene, or a hexakis-(aminothienyl) benzene, e.g., a hexakis-[(diarylamino)thienyl]benzene.

In another aspect, the invention features a compound of formula I

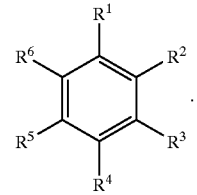

Each of $R^1$–$R^6$ is, independently,

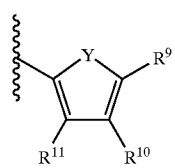

in which Y is O, S, or NH. Each of $R^9$–$R^{11}$ is, independently, H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-20}$ aryl, or substituted or unsubstituted $C_{4-20}$ heteroaryl. Alternatively, each of $R^9$–$R^{11}$ is OH, $C_{1-6}$ alkoxy, or $N(R^{12})(R^{13})$. For $N(R^{12})(R^{13})$, each of $R^{12}$ and $R^{13}$ is, independently, H, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{6-20}$ aryl. Each of $R^9$–$R^{11}$ can also be $NO_2$, CN, or $CO_2R^{14}$, in which $R^{14}$ is H or $C_{1-6}$ alkyl.

In some preferred embodiments, each of $R^{10}$ and $R^{11}$ is H. In other preferred embodiments, $R^9$ is $N(R^{12})(R^{13})$, and each of $R^{12}$ and $R^{13}$ is, independently, substituted or unsubstituted aryl, e.g., phenyl, tolyl, naphthyl, or pyrenyl. In still other preferred embodiments, $R^9$ is carbazolyl.

Preferably, Y is S. For example, each of $R^1$–$R^6$ can have one of the following formulae:

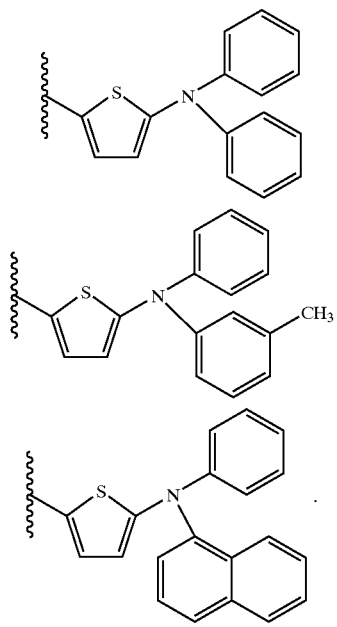

In another aspect, the invention features an electroluminescence device made with one or more of the compounds described above. The device includes a substrate, which may be coated. The device also includes a hole transporting layer, an emitting layer, and an electron transporting layer. The compounds described above may be included in the hole transporting layer and/or the emitting layer.

The term "saturated" used herein refers to a compound or portion of a compound having each atom either hydrogenated or substituted such that the valency of each atom is filled.

The term "unsaturated" used herein refers to a compound or portion of a compound where the valency of each atom may not be filled with hydrogen or other substituents. For example, adjacent carbon atoms can be doubly bound to each other.

The term "substituted" used herein refers to moieties having one, two, three or more substituents, which may be the same or different, each replacing a hydrogen atom. Examples of substituents include but are not limited to alkyl, hydroxyl, protected hydroxyl, amino, protected amino, carboxy, protected carboxy, cyano, alkoxy, and nitro.

The term "unsubstituted" used herein refers to a moiety having each atom hydrogenated such that the valency of each atom is filled.

The term "aryl" used herein refers to a moiety having a hydrocarbon ring system (e.g., a fused ring system) having at least one aromatic ring. Examples of aryl moieties include, but are not limited to, phenyl, naphthyl, and pyrenyl.

The term "heteroaryl" used herein refers to a moiety having a ring system (e.g., a fused ring system) with at least one aromatic ring and at least one heteroatom, including, but not limited to, O, N, and S. Examples of heteroaryl moieties include, but are not limited to, pyridinyl, carbazolyl, and indolyl.

Protected forms of the compounds described herein are included within the scope of the invention. In general, the species of protecting group is not critical, provided that it is stable to the conditions of any subsequent reaction(s) on other positions of the compound and can be removed at the appropriate point without adversely affecting the remainder of the molecule. In addition, one protecting group may be substituted for another after substantive synthetic transformations are complete. Examples and conditions for the attachment and removal of various protecting groups are found in T. W. Greene, Protective Groups in Organic Chemistry, (1st ed., 1981, 2nd ed., 1991).

In addition, salts of the compounds described herein are within the scope of the invention. For example, a salt can be formed between a positively charged amino substituent and a negatively charged counterion.

The details of several embodiments of the invention are set forth in the accompanying drawings and the description below. Other features, objects, and advantages of the invention will be apparent from the description and drawings, and from the claims.

DETAILED DESCRIPTION

The invention features methods for preparing hexasubstituted benzene compounds, the compounds themselves, and EL devices made using these compounds. In particular, the invention features methods for the six-fold substitution of a hexahalobenzene. For example, a hexakis(thienyl)benzene can be synthesized by the palladium-catalyzed thienylation of hexabromobenzene. These starburst-shaped compounds can help improve the physical properties of the organic LEDs into which they are incorporated.

A method for synthesizing a hexaarylbenzene is as follows: If the aryl group is to be substituted, a substituted aryl or heteroaryl compound is first prepared. The substituted aryl or heteroaryl compound may be prepared by coupling a halogenated aryl or heteroaryl compound with a substituent in the presence of a catalyst, e.g., CuI. Examples of substituents include alkyl, aryl, amino, alkoxy, hydroxy, carboxy, nitro, and cyano substituents. The resulting compound is then converted to a metallated compound, e.g., an aryl zinc chloride, a heteroaryl zinc chloride, an aryl stannane, or a heteroaryl stannane. A hexahalobenzene is then contacted with the metallated compound, or a mixture of such compounds, in the presence of a catalyst. The result is a hexasubstituted benzene.

Shown below in the scheme is a synthetic procedure for making exemplary compounds of the invention, indicated as compounds 4a–4d.

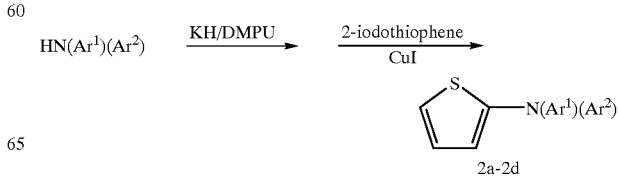

2a–2d

-continued 1a, carbazole
1b, Ar¹ = Ph; Ar² = 3-tolyl
1c, Ar¹ = Ph; Ar² = 1-naphthyl
1d, Ar¹ = Ar² = Ph

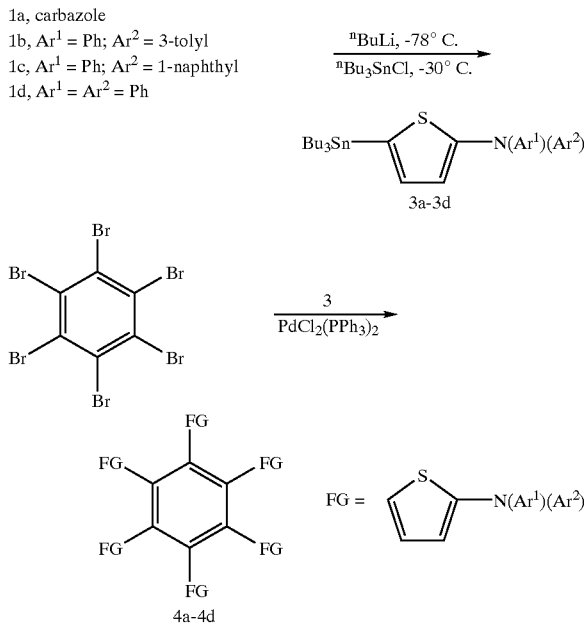

4a–4d

As shown in the scheme, Ullmann coupling of iodothiophene with diarylamines 1a–1d affords diarylthienylamines 2a–2d. Amines 2a–2d are then converted to thienylstannanes 3a–3d. (P. V. Bedworth, Y Cai, A. Jen, S. R. Marder, *J. Org. Chem.* 1996, 61, 2242) Sixfold thienylation of hexabromobenzene with thienylstannanes 3a–3d, using Stille's cross-coupling reactionn (Stille, J. K., *Angew. Chem. Int. Ed.* 1986, 25, 508) yields air-stable starburst compounds 4a–4d.

Hexaarylbenzene derivatives are useful as organic EL materials for a variety of reasons. The expected twisting of the aryl units to the central benzene may hinder close packing of the molecules in the solid state, and facilitate formation of stable amorphous morphology. In addition, the high local concentration of functional groups, which may act as hole transporting units, may be beneficial to the physical performance of the materials. For example, the concentration may promote current flux.

The electronic properties of the aryl groups are important as well. For example, the π-excessive thiophene ring may lower the oxidation potential of the compound to which it is attached.

The compounds of the invention can be used to make electroluminescence devices. A diagrammatic representation of such a device is shown below.

Multiple Layer Device

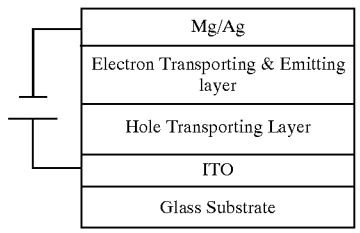

Electroluminescence devices generally include multiple layers. A typical device includes a substrate, e.g., glass, which may be coated with an oxide, e.g., indium-tin-oxide (ITO). The device also includes a hole transporting layer, an electron transporting layer, and an emitting layer. The hole transporting layer and the emitting layer may be combined into a single layer, or the emitting layer and the electron transporting layer may be combined into a single layer. The device may also include a cathode.

Devices can be prepared by vacuum deposition of compounds 4a–4d (as hole transporting layer), followed by Alq₃ as emitting layer and electron-transporting layer (Alq₃=tris (8-quinolinolato)aluminum (III), C. W. Tang, S. A. VanSlyke, *Appl. Phys. Lett.* 1987, 51, 913; J. Kido, Y. Lizumi, *Chem. Lett.* 1997, 963) onto an indium-tin-oxide (ITO) coated glass substrate. An alloy of magnesium and silver (ca. 8:1, 500 Å), which serves as the cathode, can be deposited onto the organic layer by simultaneously evaporating from two different sources. The cathode is capped with 1000 Å of silver. The current-voltage (I-V) curve can be measured on a Keithley 2000 Source Meter in an ambient environment. Light intensity (L) is measured with a Newport 1835 Optical Meter.

Without further elaboration, it is believed that one skilled in the art can, based on the description herein, utilize the present invention to its fullest extent. All publications recited herein are hereby incorporated by reference in their entirety. The following specific examples, which describe the synthesis of various compounds of the invention, are therefore to be construed as merely illustrative, and not limitative of the remainder of the disclosure in any way.

EXAMPLE 1

Synthesis of 9-(2-thienyl)-9H-carbazole (2a) and 9-[5-(1,1,1-tributyl-stannyl)-2-thienyl]-9H-carbazole (3a)

Compounds 9-(2-thienyl)-9H-carbazole (2a) and 9-[5-(1,1,1-tributyl-stannyl)-2-thienyl]-9H-carbazole (3a) were synthesized using the same procedures used to synthesize 2-(N,N-diphenylamino)thiophene and 5-(tributylstannyl)-2-(diphenylamino)thiophene, as described in P. V. Bedworth, Y Cai, A. Jen, S. R. Marder, *J. Org. Chem.* 1996, 61, 2242 except that carbazole (1a) was utilized instead of diphenylamine.

EXAMPLE 2

Synthesis of 9-(4-{2,3,4,5,6-penta[5-(9H-9-carbazol-yl)-2-thienyl]phenyl}-2-thienyl)-9H-carbazole (4a)

To a flask containing the crude 3a (0.84 g, 1.32 mmol, 85% purity), hexabromobenzene (0.11 g, 0.20 mmol) and PdCl₂(PPh₃)₂ (21 mg, 0.030 mmol) was added 10 mL of N,N-dimethylformamide. The solution was stirred at 80° C. for 30 min, then 16 hours at 60° C., and then cooled. Methanol (20 mL) was added to precipitate the product and the ppt was recrystallized from CH₂Cl₂/hexane to give a white powdery compound (4a) (0.22 g, 85%).

¹H NMR (300 MHz, CDCl₃, TMS): δ=8.06 (d, 12H, J=7.6 Hz, C₆H₄), 7.26 (d, 12 H, J=8.2 Hz, C₆H₄), 7.20 (dd, 12H, J=7.6, 7.4 Hz, C₆H₄), 7.11 (d, 6H, J=3.6 Hz, SCCH), 7.06 (d, 6H, J=3.6 Hz, SCCH), 7.02 (dd, 12H, J=8.2, 7.4 Hz, C₆H₄); MS (FAB): m/z 1560 (M⁺); elemental analyses: calcd: C, 78.43; H, 3.87; N, 5.38; found: C, 78.24; H, 4.08; N, 5.51.

Compound 4a is crystalline and melts at 392° C. Its high decomposition temperature 590° C.) rivals that of some polycyclic aromatic hydrocarbons. (F. Morgenroth, E. Reuther, K. Müllen, *Angew. Chem. Int. Ed. Engl.* 1997, 36, 631; M. Müller, S. I. Vivekanantan, C. Kübel, V. Enkelmann, K. Müllen, *Angew. Chem. Int. Ed. Engl.* 1997, 36, 1607.)

EXAMPLE 3

Synthesis of N2-(3-methylphenyl)-N2-phenyl-5-(2,3,4,5,6-penta{5-[3-methyl(phenyl)anilino]-2-thienyl}phenyl) 2-thiophenamine (4b)

The basic procedure used to make 4a was followed for the synthesis of compound 4b. Compound 4b was produced in 63% yield; the compound was a pale yellow powder.

$^1$H NMR (300 MHz, CDCl$_3$, TMS): δ=7.08 (dd, 12H, J=8.4, 7.2 Hz, meta-H of C$_6$H$_5$), 7.02 (dd, 12H, J=8.4, 1.3 Hz, ortho-H of C$_6$H$_5$), 6.98 (dd, 6H, J=7.7, 7.4 Hz, 5-H of C$_6$H$_4$Me), 6.87 (tt, 6H, J=7.2, 1.3 Hz, para-H of C$_6$H$_5$), 6.84 (s, 6H, 2-H of C$_6$H$_5$), 6.83 (d, 6H, J=7.7 Hz, 4-H of C$_6$H$_4$Me), 6.81 (d, 6H, J=7.4 Hz, 6-H of C$_6$H$_4$Me), 6.46 (d, 6H, J=3.6 Hz, J=3.6 Hz, SCCH), 6.42 (d, 6H, J=3.6 Hz, SCCH), 2.10 (s, 18H, CH$_3$); MS (FAB): m/z 1656 (M$^+$); elemental analyses: calcd: C, 78.22; H, 5.11; N, 5.07; found: C, 78.08; H 5.26, N, 5.22.

EXAMPLE 4

Synthesis of N2-(1-naphthyl)-N2-phenyl-5-(2,3,4,5,6-penta{5-[1-naphthylanilino]-2-thienyl}phenyl) 2-thiophenamine (4c)

The basic procedure used to make 4a was followed for the synthesis of compound 4c. Compound 4c was produced in 91% yield, as a yellow powder.

$^1$H NMR (300 MHz, CDCl$_3$, TMS): δ=7.87 (d, 6H, J=8.4, naph) 7.77 (d, 6H, J=8.2 Hz, naph), 7.65 (dd, 6H, J=7.6, 1.2 Hz, naph), 7.33 (ddd, 6H, J=8.2, 7.2, 1.2 Hz, naph), 7.26–7.15 (m, 18H, naph), 7.01 (dd, 12H, J=7.7, 7.7 Hz, meta-H of C$_6$H$_5$), 6.83 (dd, 12H, J=7.7, 1.1 Hz, ortho-H of C$_6$H$_5$), 6.80 (tt, 6H, J=7.7, 1.1 Hz, para-H of C$_6$H$_5$), 6.25 (d, 6H, J=4.0 Hz, SCCH), 6.23 (d, 6H, J=4.0 Hz, SCCH); MS (FAB): m/z 1872 (M$^+$); elemental analyses: calcd: C, 80.74; H, 4.52; N, 4.48; found; C, 80.90; H, 4.71; N, 4.30.

EXAMPLE 5

Synthesis of N2,N2-diphenyl-5-(2,3,4,5,6-penta{5-[1phenylanilino]-2-thienyl}phenyl)2-thiophenamine (4d)

The basic procedure used to make 4a was followed for the synthesis of compound 4d. Compound 4d was produced in 91% yield, as a yellow powder.

$^1$H NMR (300 MHz, CDCl$_3$, TMS): δ=7.11 (dd, 24H, J=7.8, 7.2 Hz, meta-H of C$_6$H$_5$), 7.02 (dd, 24H, J=7.8, 1.2 Hz, ortho-H of C$_6$H$_5$), 6.90 (tt, 12H, J=7.2, 1.2 Hz, para-H of C$_6$H$_5$), 6.45 (d, 6H, J=4.0 Hz, SCCH), 6.42 (d, 6H, J=4.0 Hz, C$_6$H$_4$); MS (FAB): m/z 1572 (M$^+$); elemental analyses: calcd: C, 77.83; H, 4.61; N, 5.34; found: C, 77.39; H, 4.70; N, 5.04.

Compounds 4b-4d were a morphous and formed stable glasses, as shown below in Table 1. They were thermally stable (T$_d$379–473° C.) and had higher T$_g$ (glass transition temperature) values than benzidine analogues 1,4-bis (diphenylamino)-biphenyl (T$_g$=77° C.), 1,4-bis(1-naphthylphenylamino)biphenyl (α-NPD, T$_g$=100° C.), and 1,4-bis(phenyl-m-tolylamino)biphenyl (TPD, T$_g$=60° C.). Both α-NPD and TPD are commonly used as hole transporting materials in organic light emitting devices.

EXAMPLE 6

Preparation of electroluminescence devices using compounds 4a-4d

Devices were prepared by vacuum deposition of 400 Å of compounds 4a-4d (as hole transporting layer), followed by 400 Å of Alq$_3$ as emitting layer and electron-transporting layer (Alq$_3$=tris(8-quinolinolato)aluminum (C ), C. W. Tang, S. A. VanSlyke, *App. Phys. Lett.* 1987, 51:913; J. Kido, Y. Lizumi, *Chem. Lett.* 1997, 963) onto an indium-tin-oxide (ITO) coated glass substrate. The deposition rate was 2–5 Å/s at 2×10$^{-5}$ Torr. An alloy of magnesium and silver (ca. 8:1, 500 Å), which served as the cathode, was deposited onto the organic layer by simultaneously evaporating from two different sources. The cathode was capped with 1000 Å of silver. For comparison, a device using 1,4-bis(1-naphthylphenylamino)biphenyl (NPD) as the hole transporting layer was also prepared.

EXAMPLE 7

Results

Current-voltage (I-V) curves were measured on a Keithley 2000 Source Meter in an ambient environment. Light intensity (L) was measured with a Newport 1835 Optical Meter.

The I-V-L characteristics of the devices described above were determined. In all cases, green light emission from Alq$_3$ at 520 nm was observed. While these devices are not optimized, it is seen that with the same device structure, performance characteristics such as turn on voltage (6–8 V), maximum luminescence (14000–20000 cd/m$^2$) and external quantum efficiency (1.2–1.6%) of device s composed using the compounds of the invention are similar to those of the standard device (7 V, 25000 cd/m$^2$, 1.3%). This confirms that such materials can be used in fabricating EL devices.

From cyclic voltammetry (CV) and Osteryoung square wave voltammetry (OSWV) measurements, compounds 4a–d were found to exhibit a quasi-reversible six-electron redox process (as shown in Table 1), corresponding to removal of an electron from each of the diarylamines. The oxidation potential increased in the order of 4b (159 mV)<4d (164 mV)<4c (176 mV)<<4a (717 mV). This order may be due to the relative electron-withdrawing ability of the arenes to the nitrogen. Significantly, the oxidation potential of 4b was lower than that of TPD (ΔE$_{ox}$=155 mV), and the corresponding potential of 4c was less than that of Δ-NPD (ΔE$_{ox}$=166 mV). This outcome mostly likely stems from the incorporation of an electron rich thienyl ring to the nitrogen atom.

TABLE 1

Physical data for Compounds 4a–4d, TPD, and NPD.

| Compd | T$_g$/T$_m$, ° C. [a] | T$_d$, ° C. [b] | λ$_{max}$, nm [c] | E$_{ox}$ (ΔE$_p$), mV [d] |
|---|---|---|---|---|
| 4a | NA/392 | 569 | 292, 334 | 717 (60) |
| 4b | 80/NA$^a$ | 379 | 297, 350 sh | 159 (109) |
| 4c | 111/NA$^a$ | 463 | 354 | 176 (72) |
| 4d | 96/N$^a$ | 399 | 293, 350 sh | 164 (81) |
| TPD | 60/175 | 382 | 311, 353 | 314 (68) |
| NPD | 100/265$^a$ | 479 | 271, 342 | 242 (66) |

[a] obtained from DSC measurements; NA: T$_g$ or T$_m$ not detected. [b] obtained from TGA measurements. [c] measured in CH$_2$Cl$_2$ solution; [d] measured in CH$_2$Cl$_2$/CH$_3$CN (1:1). All E$_{ox}$ data are reported relative to ferrocene which has an E$_{ox}$ at 223 mV relative to Ag/Ag+ and the anodic peak-cathodic peak separation (ΔE$_p$) is 75 mV. The concentration of the complexes used in this experiment was 5 × 10$^{-4}$ M and the scan rate was 80 mV s$^{-1}$.

To obtain the data presented in Table 1, DSC measurements were carried out using a Perkin Elmer 7 series thermal analyzer at a heating rate of 10 degree/min. TGA measurements were performed on a Perkin Elmer TGA7 thermal analyzer. Electronic absorption spectra were obtained on a Perkin-Elmer Lambda 9 spectrometer. Cyclic voltammetry (CV) and Osteroung square wave voltammetry (ferrocene as internal standard) measurements were carried out in a three electrode and potentiostat configuration on a Bioanalytical System BAS 100B.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Accordingly, other embodiments are within the scope of the following claims.

What is claimed is:

1. A compound of formula I

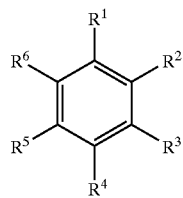

wherein
each of $R^1$–$R^6$ is, independently,

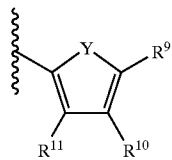

in which Y is O, S, or NH,
and each of $R^9$–$R^{11}$ is, independently, H, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{6-20}$ aryl, substituted or unsubstituted $C_{4-20}$ heteroaryl, OH, $C_{1-6}$ alkoxy, $N(R^{12})(R^{13})$, in which each of $R^{12}$ and $R^{13}$ is, independently, H, substituted or unsubstituted $C_{1-6}$ alkyl, substituted or unsubstituted $C_{2-6}$ alkenyl, substituted or unsubstituted $C_{2-6}$ alkynyl, or substituted or unsubstituted $C_{6-20}$ aryl, $NO_2$, CN, or $CO_2R^{14}$, in which $R^{14}$ is H or $C_{1-6}$ alkyl.

2. The compound of claim 1, wherein each of $R^{10}$ and $R^{11}$ is H.

3. The compound of claim 2, wherein $R^9$ is $N(R^{12})(R^{13})$.

4. The compound of claim 3, wherein each of $R^{12}$ and $R^{13}$ is, independently, substituted or unsubstituted aryl.

5. The compound of claim 4, wherein each of $R^{12}$ and $R^{13}$ is, independently, selected from the group consisting of phenyl, tolyl, naphthyl, and pyrenyl.

6. The compound of claim 2, wherein $R^9$ is carbazolyl.

7. The compound of claim 1, wherein Y is S.

8. The compound of claim 1, wherein each of $R^1$–$R^6$ has the following formula:

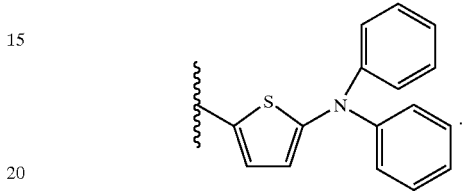

9. The compound of claim 1, wherein each of $R^1$–$R^6$ has the following formula:

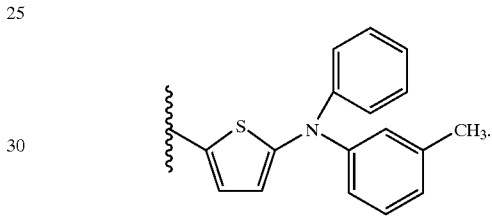

10. The compound of claim 1, wherein each of $R^1$–$R^6$ has the following formula:

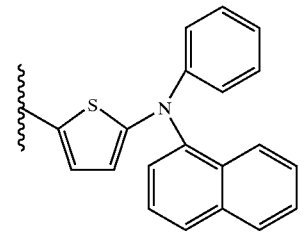

* * * * *